(12) United States Patent
Nallaperumal et al.

(10) Patent No.: US 12,704,492 B2
(45) Date of Patent: Aug. 11, 2026

(54) METHOD TO PROVIDE LOCALIZED VOICE SERVICE

(71) Applicant: Carrier Corporation, Palm Beach Gardens, FL (US)

(72) Inventors: Pirammanayagam Nallaperumal, Hyderabad (IN); Govardhan Reddy Pagidi, Hyderabad (IN)

(73) Assignee: KIDDE FIRE PROTECTION, LLC, Bradenton, FL (US)

( * ) Notice: Subject to any disclaimer, the term of this patent is extended or adjusted under 35 U.S.C. 154(b) by 543 days.

(21) Appl. No.: 18/314,550

(22) Filed: May 9, 2023

(65) Prior Publication Data

US 2023/0366865 A1 Nov. 16, 2023

Related U.S. Application Data

(60) Provisional application No. 63/340,260, filed on May 10, 2022.

(51) Int. Cl.

| | |
|---|---|
| ***G01N 33/00*** | (2006.01) |
| ***G06F 3/16*** | (2006.01) |
| ***H04W 4/021*** | (2018.01) |
| ***H04W 4/33*** | (2018.01) |

(52) U.S. Cl.

CPC ......... *G01N 33/0075* (2013.01); *G06F 3/167* (2013.01); *H04W 4/021* (2013.01); *H04W 4/33* (2018.02)

(58) Field of Classification Search

CPC .... G01N 33/0075; H04W 4/33; H04W 4/021; G06F 3/167

See application file for complete search history.

(56) References Cited

U.S. PATENT DOCUMENTS

| | | | |
|---|---|---|---|
| 6,970,077 B2 | 11/2005 | Johnson et al. | |
| 7,109,879 B2 | 9/2006 | Stults et al. | |
| 7,135,965 B2 | 11/2006 | Chapman, Jr. et al. | |
| 7,242,288 B2 | 7/2007 | Kaiser et al. | |
| 7,752,047 B2 * | 7/2010 | Morris .................... | G10L 15/26 704/274 |

(Continued)

FOREIGN PATENT DOCUMENTS

| | | |
|---|---|---|
| EP | 2933789 A1 | 10/2015 |
| WO | 0022591 A1 | 4/2000 |
| WO | 2021079215 A1 | 4/2021 |

OTHER PUBLICATIONS

Unknown, "Airthings 2930 Wave Plus—Radon & Air Quality Monitor (CO2, Voc, Humidity, Temp, Pressure)", Amazon, date unknown.

(Continued)

*Primary Examiner* — Catherine T. Rastovski
*Assistant Examiner* — Nyla Gavia
(74) *Attorney, Agent, or Firm* — CANTOR COLBURN LLP

(57) ABSTRACT

A method of monitoring and reporting an environmental parameter, the method including receiving a request for the environmental parameter from a first individual using a voice activated assistant device; detecting a location of the first individual, the location including a room that the first individual is located in; detecting the environmental parameter using an environmental sensor nearest to the first individual; and conveying the environmental parameter to the first individual.

12 Claims, 3 Drawing Sheets

(56) References Cited

U.S. PATENT DOCUMENTS 7,957,974 B2 6/2011 Cho et al.
8,175,884 B1 5/2012 Morris
8,234,120 B2 7/2012 Agapi et al.
8,412,532 B2 4/2013 Gruenstein et al.
8,825,020 B2 9/2014 Mozer et al.
8,988,232 B1 * 3/2015 Sloo ...................... G01J 1/4204 340/602
9,384,751 B2 7/2016 Venkatesha et al.
9,454,893 B1 9/2016 Warren et al.
9,472,205 B2 10/2016 Kolavennu et al.
9,520,042 B2 * 12/2016 Eck .......................... G08B 3/10
9,593,861 B1 3/2017 Burnett
9,697,700 B2 7/2017 Schmidt et al.
9,860,076 B2 1/2018 Warren
9,934,658 B1 4/2018 Field
10,049,670 B2 8/2018 Wang et al.
10,078,959 B2 9/2018 Rossi et al.
10,127,926 B2 11/2018 James
10,133,443 B2 11/2018 Von Dehsen et al.
10,145,579 B2 12/2018 Stoner et al.
10,313,531 B2 6/2019 Warrick
10,614,804 B2 4/2020 Kolavennu et al.
10,767,876 B2 9/2020 Kelly et al.
10,837,667 B2 11/2020 Nelson et al.
10,884,096 B2 1/2021 Baek et al.
11,100,929 B2 8/2021 Bradley et al.
2006/0147003 A1 7/2006 Archack, Jr. et al.
2011/0037599 A1 * 2/2011 Johnson, Jr. ....... G08B 13/2462 340/632
2015/0097687 A1 * 4/2015 Sloo ......................... F24F 11/34 340/632
2019/0114904 A1 4/2019 Subramanian

OTHER PUBLICATIONS

Unknown, “Introducing Amazon Smart Air Quality Monitor—Know your air, Works with Alexa—A Certified for Humans Device”, Amazon, date unknown.

* cited by examiner

METHOD TO PROVIDE LOCALIZED VOICE SERVICE

CROSS-REFERENCE TO RELATED APPLICATIONS

This application claims the benefit of U.S. Provisional Application No. 63/340,260 filed May 10, 2022, all of which is incorporated herein by reference in their entirety.

BACKGROUND

The embodiments herein generally relate to environmental sensors and more specifically, a method and apparatus to provide an environmental parameter detected by environmental sensors.

Environmental parameters are an important factor to create a safer indoor living environment. Example environmental parameters may include smoke, fire, carbon monoxide levels, indoor air quality, etc. Indoor air quality devices such as, air purifiers, air conditioners, humidifiers, dehumidifier, and ventilators are often used to control environmental parameters, such as indoor air quality, but individuals are often given little feedback as to a resultant indoor air quality provided by these systems.

BRIEF DESCRIPTION

According to one embodiment, a method of monitoring and reporting an environmental parameter includes receiving a request for the environmental parameter from a first individual using a voice activated assistant device; detecting a location of the first individual, the location including a room that the first individual is located in; detecting the environmental parameter using an environmental sensor nearest to the first individual; and conveying the environmental parameter to the first individual.

In addition to one or more of the features described above, or as an alternative, further embodiments of may include wherein the conveying environmental parameter to the first individual further includes audibly providing the environmental parameter to the first individual via the voice activated assistant device.

In addition to one or more of the features described above, or as an alternative, further embodiments of may include wherein the conveying the environmental parameter to the first individual further includes displaying the environmental parameter on a computing device of the first individual.

In addition to one or more of the features described above, or as an alternative, further embodiments of may include wherein the detecting the location of the first individual further includes detecting a wireless advertisement of a computing device of the first individual using the environmental sensor.

In addition to one or more of the features described above, or as an alternative, further embodiments of may include wherein the wireless advertisement is a Bluetooth signal.

In addition to one or more of the features described above, or as an alternative, further embodiments of may include wherein the environmental sensor includes one or more of a smoke detector, fire detector, carbon monoxide detector and an indoor air quality detector.

According to another embodiment, a method of monitoring and reporting an environmental parameter includes receiving a request for the environmental parameter from a first individual using a voice activated assistant device; detecting a location of a second individual, the location including a room that the second individual is located in; detecting the environmental parameter using an environmental sensor nearest to the second individual; and conveying the environmental parameter to the first individual.

In addition to one or more of the features described above, or as an alternative, further embodiments of may include wherein the conveying the environmental parameter to the first individual further includes audibly providing the environmental parameter to the first individual via the voice activated assistant device.

In addition to one or more of the features described above, or as an alternative, further embodiments of may include wherein the conveying the environmental parameter to the first individual further includes displaying the environmental parameter on a computing device of the first individual.

In addition to one or more of the features described above, or as an alternative, further embodiments of may include wherein the detecting the location of the second individual further includes detecting a wireless advertisement of a computing device of the second individual using the environmental sensor.

In addition to one or more of the features described above, or as an alternative, further embodiments of may include wherein the wireless advertisement is a Bluetooth signal.

In addition to one or more of the features described above, or as an alternative, further embodiments of may include wherein the environmental sensor includes one or more of a smoke detector, fire detector, carbon monoxide detector and an indoor air quality detector.

According to another embodiment, a computer program product tangibly embodied on a non-transitory computer readable medium includes instructions that, when executed by a processor, cause the processor to perform operations including receiving a request for an environmental parameter from a first individual using a voice activated assistant device; detecting a location of the first individual, the location including a room that the first individual is located in; detecting the environmental parameter an environmental sensor nearest to the first individual; and conveying the environmental parameter to the first individual.

In addition to one or more of the features described above, or as an alternative, further embodiments of may include wherein the conveying the environmental parameter to the first individual further includes audibly providing the environmental parameter to the first individual via the voice activated assistant device.

In addition to one or more of the features described above, or as an alternative, further embodiments of may include wherein the conveying the environmental parameter to the first individual further includes displaying the environmental parameter on a computing device of the first individual.

In addition to one or more of the features described above, or as an alternative, further embodiments of may include wherein the detecting the location of the first individual further includes detecting a wireless advertisement of a computing device of the first individual using the environmental sensor.

In addition to one or more of the features described above, or as an alternative, further embodiments of may include wherein the wireless advertisement is a Bluetooth signal.

In addition to one or more of the features described above, or as an alternative, further embodiments of may include wherein the environmental sensor includes one or more of a smoke detector, fire detector, carbon monoxide detector and an indoor air quality detector.

Technical effects of embodiments of the present disclosure include monitoring a location of an individual, tracking the environmental parameter(s) in a location and then providing the environmental parameters(s) to the individual after the individual request it using a voice activated assistant.

The foregoing features and elements may be combined in various combinations without exclusivity, unless expressly indicated otherwise. These features and elements as well as the operation thereof will become more apparent in light of the following description and the accompanying drawings. It should be understood, however, that the following description and drawings are intended to be illustrative and explanatory in nature and non-limiting.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

The embodiments of the method and apparatus detailed herein relate to a method to provide one or more environmental parameters to a user when requested via a voice activated assistant.

Figure 1:
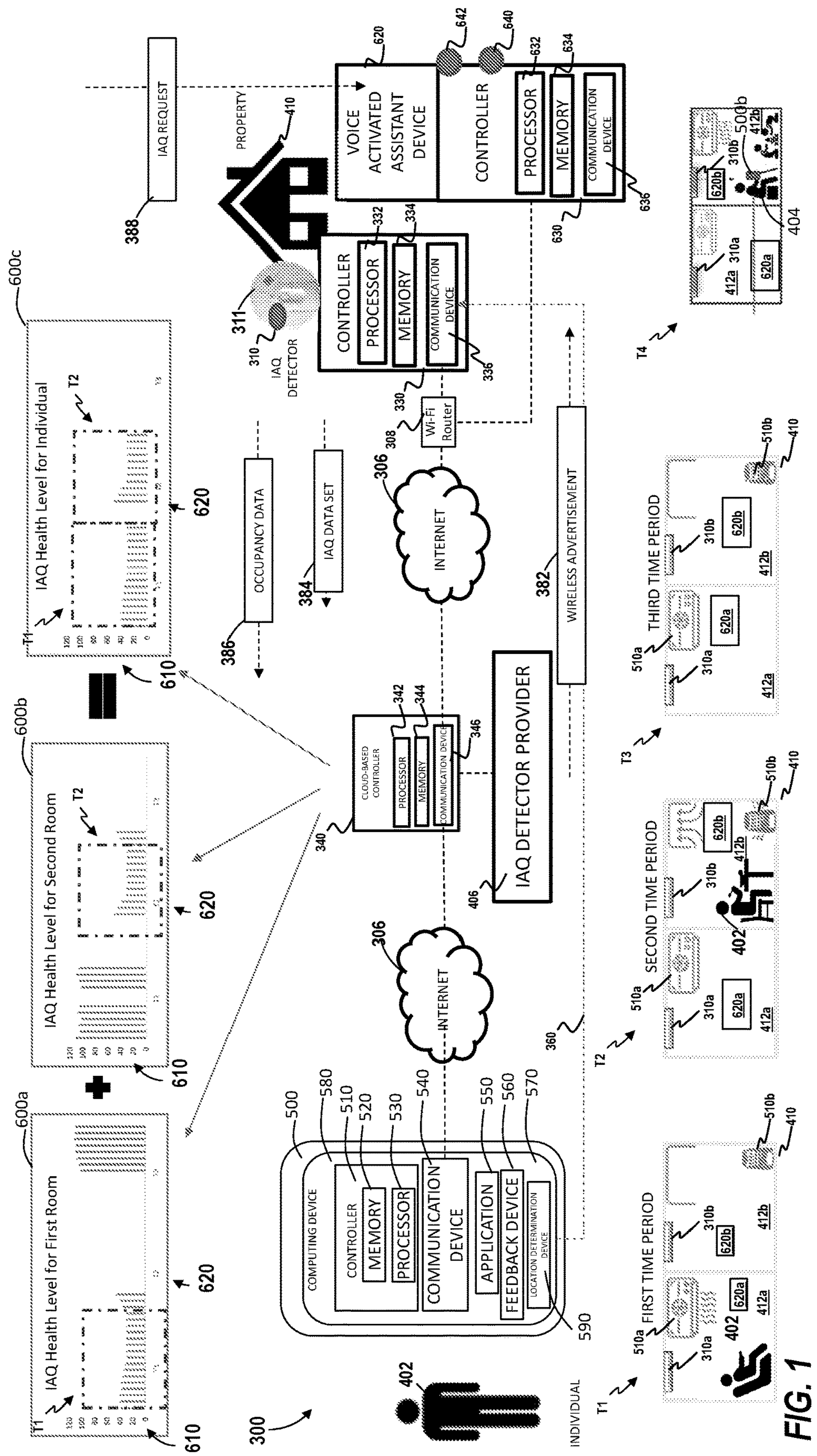
FIG. 1 is a schematic diagram of an indoor air quality (IAQ) detector system, according to an embodiment of the present disclosure.

Referring now to FIG. 1, a schematic diagram of an IAQ detector system 300 is illustrated, according to an embodiment of the present disclosure. It should be appreciated that, although particular systems are separately defined in the schematic block diagrams, each or any of the systems may be otherwise combined or separated via hardware and/or software.

Figure 2:
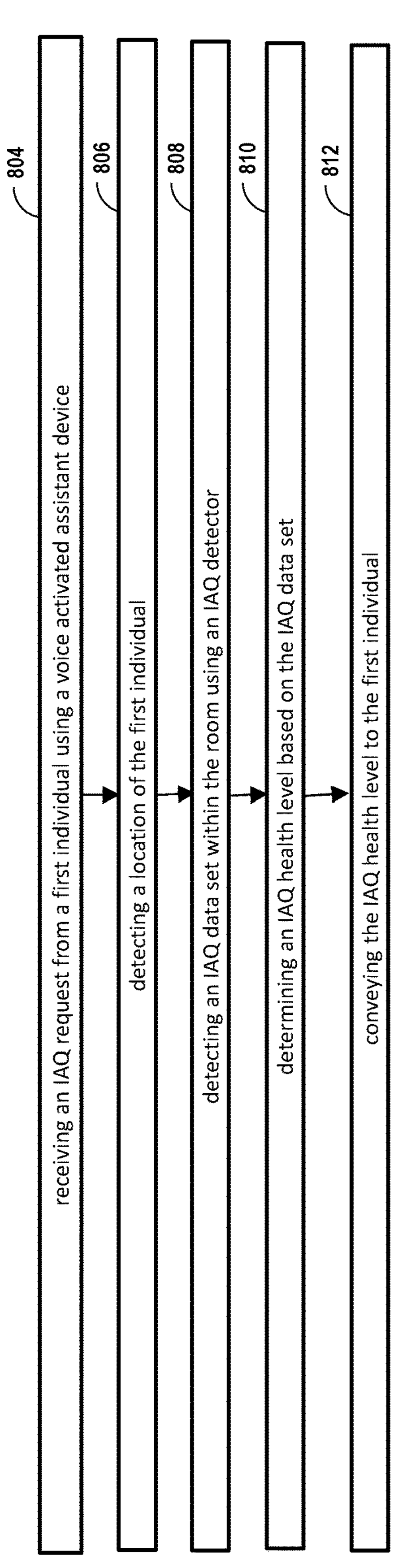
FIG. 2 is a flow process illustrating a method of monitoring and reporting an IAQ level, according to an embodiment of the present disclosure.
Figure 3:
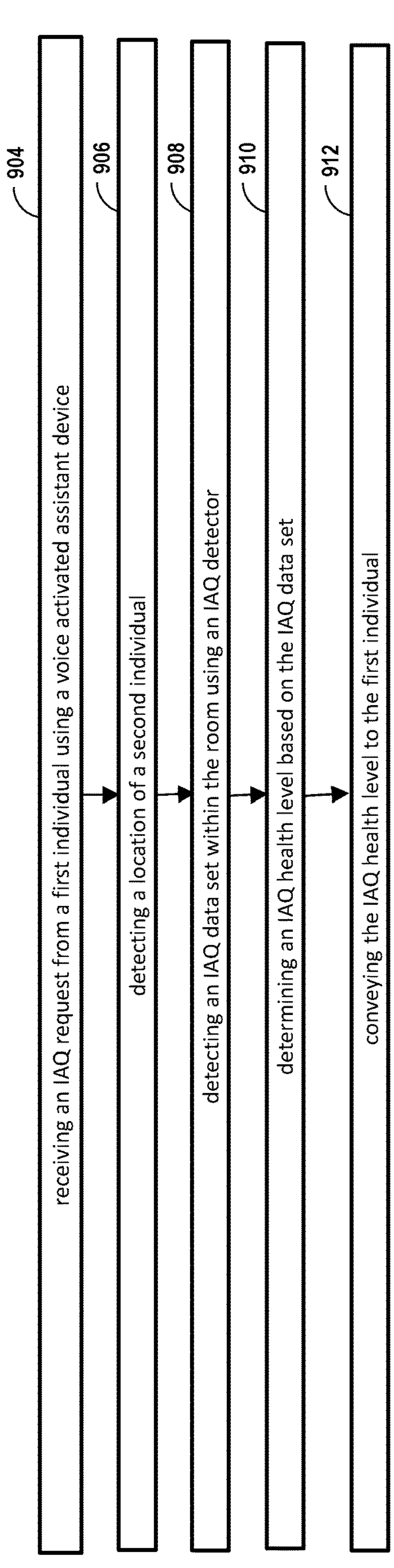
FIG. 3 is a flow process illustrating a method of monitoring and reporting an IAQ level, according to an embodiment of the present disclosure.

FIGS. 1-3 are directed to providing an IAQ parameter to a user. It is understood that the IAQ detector 310 of FIG. 1 is one example of an environmental sensor. Embodiments may use a variety of environmental sensors (e.g., smoke detector, fire detector, carbon monoxide detector, IAQ detector) to provide a variety of environmental parameters to a user. Embodiments are not limited to an IAQ detector and reporting the IAQ level, which are described with reference to FIGS. 1-3 as an example embodiment.

The IAQ detector system 300 includes the cloud-based controller 340, an IAQ detector 310 and a computer application 550 installed or accessible to a computing device 500. The computer application 550 may be accessible from the computing device 500, such as, for example, a software-as-as service or a website. The computer application 550 may be in communication with the cloud database via the internet 306.

The IAQ detector 310 may be configured to detect an IAQ within the property 410. The IAQ detector 310 may be located within a fire detector 311 or may be the fire detector 311. The fire detector 311 may be a smoke detector, a $CO_2$ detector, a CO detector, a heat sensor, or any other IAQ detector known to one of skill in the art. The IAQ detector 310 and/or the fire detector 311 may be an internet of things (IoT) connected device. The property 410 may be a home, an apartment, a garage, a room, a shed, a storage unit, a car, a vehicle, land, or any other area known to one of skill in the art that may need to be protected from fire. The property 410 may be owned by an individual 402, rented by the individual 402, in possession of an individual 402, in control of the individual 402, leased by the individual 402, or mortgaged by the individual 402. The individual 402 may be a person, an organization, a group, a partnership, a company, or a corporation.

The property 410 may have one or more IAQ detectors 310. The one or more IAQ detectors 310 may each be in communication with each other. In an embodiment there may be at least one IAQ detector 310 located in each room of the property 410. The property may include multiple rooms 412*a*, 412*b*. In the illustrated example of FIG. 1, the property 410 includes a first room 412*a* and a second room 412*b*.

The first room 412*a* includes a first IAQ detector 310*a* and a first IAQ device 510*a*. The first IAQ detector 310*a* is configured to detect an IAQ within the first room 412*a*. The first IAQ device 510*a* is configured to adjust an internal air quality within the first room 412*a*. The first IAQ device 510*a* may be an air purifier, an air conditioner, a humidifier, a dehumidifier, a ventilator, and/or any other IAQ device known to one of skill in the art.

The second room 412*b* includes a second IAQ detector 310*b* and a second IAQ device 510*b*. The second IAQ detector 310*b* is configured to detect an IAQ within the second room 412*b*. The second IAQ device 510*b* is configured to adjust an internal air quality within the second room 412*b*. The second IAQ device 510*b* may be an air purifier, an air conditioner, a humidifier, a dehumidifier, a ventilators and/or any other IAQ device known to one of skill in the art.

There may also be one or more IAQ devices 510*a*, 510*b* located in each room. The IAQ devices 510*a*, 510*b* may be the same or different across different rooms 412*a*, 412*b*.

IAQ detectors 310 may be used to simultaneously refer to the first IAQ detector 310*a* and the second IAQ detector 310*b* herein. It is understood that while two IAQ detectors 310 are described and illustrated herein, the embodiments disclosed herein may be applicable to one or more IAQ detectors 310 in a property 410.

The IAQ detector system 300 may also include a voice activated assistant device 620. The voice activated device 620 may be a Google Home, an Amazon Alexa, or any other similar device. The voice activated assistant device 620 may include microphone 640 configured to detect sound waves and a speaker 642 configured to emit sound waves.

The voice activated assistant device 620 includes a controller 630 that is configured to communicate with the computer application 550 and the cloud-based controller 340. The controller 630 may be a controller dedicated solely for the voice activated assistant device 620 or shared with the fire detector 311 or IAQ detector 310. The voice activated assistant device 620 may be a standalone device or embedded in the IAQ detector 310 or the fire detector 311.

The controller 630 may be an electronic controller including a processor 632 and an associated memory 634 comprising computer-executable instructions (i.e., computer program product) that, when executed by the processor 632, cause the processor 632 to perform various operations. The processor 632 may be, but is not limited to, a single-processor or multi-processor system of any of a wide array of possible architectures, including field programmable gate array (FPGA), central processing unit (CPU), application specific integrated circuits (ASIC), digital signal processor (DSP) or graphics processing unit (GPU) hardware arranged homogenously or heterogeneously. The memory 634 may be but is not limited to a random access memory (RAM), read only memory (ROM), or other electronic, optical, magnetic or any other computer readable medium.

The controller 630 also includes a communication device 636. The communication device 636 may be capable of wireless communication including but not limited to Wi-Fi, Bluetooth, BLE, Ultra-Wideband, Zigbee, Z-Wave, Sub-GHz RF Channel, cellular, satellite, or any other wireless signal known to one of skill in the art. The communication device 636 may be configured to communicate with the cloud-based controller 340 through the internet 306. Alternatively, or additionally, the communication device 636 may be configured to communicate directly with the cloud-based controller 340. The communication device 636 may be configured to communicate with other voice activated assistant device 620 through the internet 306 or directly through wireless communication. The communication device 636 may be connected to the internet 306 through a Wi-Fi-router 308.

Each room 412*a*, 412*b* may include a voice activated assistant device 620. For example, the first room 412*a* may include a first voice activated assistant device 620*a* and the second room 412*b* may include a second voice activated assistant device 620*b*. The first voice activated assistant device 620*a* and the second voice activated assistant device 620*b* may be collectively referred to as voice activated assistant devices 620.

The computing device 500 may be configured to emit a wireless advertisement 382. The wireless advertisement 382 may be Bluetooth, Bluetooth Low Energy, Ultra-wide band, or any other short range wireless signal known to one of skill in the art. The IAQ detector 310 may be configured to detect the wireless advertisement 382 of the computing device 500.

The computing device 500 may belong to or be in possession of an individual 402 of the property 410. Detection of the wireless advertisement 382 by the IAQ 310 would mean that the computing device 500 is within range of the IAQ detector 310, which would indicate that the computing device 500 and the individual 402 is in the same room as the IAQ detector 310. For example, if the first IAQ detector 310*a* detects the wireless advertisement 382 then it would indicate that the individual 402 is within first room 412*a*. For example, if the second IAQ detector 310*b* detects the wireless advertisement 382 then it would indicate that the individual 402 is within second room 412*b*.

Alternatively, at least one of the first IAQ detector 310*a* or the second IAQ detector 310*b* may be configured to emit the wireless advertisement 382 and the computing device 500 may be configured to detect the wireless advertisement 382. Detection of the wireless advertisement 382 by the computing device 500 would mean that the computing device 500 is within range of the IAQ detector 310, which would indicate that the computing device 500 and the individual 402 is in the same room as the IAQ detector 310. For example, if the computing device 500 detects the wireless advertisement 382 of the first IAQ detector 310*a* then it would indicate that the individual 402 is within first room 412*a*. For example, if the computing device 500 detects the wireless advertisement 382 of the second IAQ detector 310*b* then it would indicate that the individual 402 is within second room 412*b*.

The IAQ detector 310 includes a controller 330 that is configured to communicate with the computer application 550 and the cloud-based controller 340. The controller 330 may be a controller dedicated solely for the IAQ detector 310 or shared with the fire detector 311. The controller 330 may be an electronic controller including a processor 332 and an associated memory 334 comprising computer-executable instructions (i.e., computer program product) that, when executed by the processor 332, cause the processor 332 to perform various operations. The processor 332 may be, but is not limited to, a single-processor or multi-processor system of any of a wide array of possible architectures, including field programmable gate array (FPGA), central processing unit (CPU), application specific integrated circuits (ASIC), digital signal processor (DSP) or graphics processing unit (GPU) hardware arranged homogenously or heterogeneously. The memory 334 may be but is not limited to a random access memory (RAM), read only memory (ROM), or other electronic, optical, magnetic or any other computer readable medium.

The controller 330 also includes a communication device 336. The communication device 336 may be capable of wireless communication including but not limited to Wi-Fi, Bluetooth, BLE, Ultra-Wideband, Zigbee, Z-Wave, Sub-GHz RF Channel, cellular, satellite, or any other wireless signal known to one of skill in the art. The communication device 336 may be configured to communicate with the cloud-based controller 340 through the internet 306. Alternatively, or additionally, the communication device 336 may be configured to communicate directly with the cloud-based controller 340. The communication device 336 may be configured to communicate with another IAQ detector 310*a* over a wired and/or wireless connection. The communication device 336 may be connected to the internet 306 through a Wi-Fi-router 308.

The cloud-based controller 340 may belong to and/or be managed by an IAQ detector provider 406, such as, for example a manufacture of the IAQ detector 310 or an aftermarket support company for the IAQ detector 310.

The cloud-based controller 340 may perform a great deal of the analytics of the IAQ data set 384 and the occupancy data 386 detected by the IAQ detector 310.

The cloud-based controller 340 may be a remote or local computer device that includes a processor 342 and an associated memory 344 comprising computer-executable instructions (i.e., computer program product) that, when executed by the processor 342, cause the processor 342 to perform various operations. The processor 342 may be, but is not limited to, a single-processor or multi-processor system of any of a wide array of possible architectures, including field programmable gate array (FPGA), central processing unit (CPU), application specific integrated circuits (ASIC), digital signal processor (DSP) or graphics processing unit (GPU) hardware arranged homogenously or heterogeneously. The memory 344 may be but is not limited to a random access memory (RAM), read only memory (ROM), or other electronic, optical, magnetic or any other computer readable medium.

The cloud-based controller 340 also includes a communication device 346. The communication device 346 may be capable of communication with the internet 306. The communication device 346 may be configured to communicate with the computing device 500 through the internet 306. The communication device 346 may be a software module that handles communications to-and-from the computer application 550 or to-and-from the controller 330.

The computing device 500 may be a desktop computer, a laptop computer, or a mobile computing device that is typically carried by a person, such as, for example a phone, a smart phone, a PDA, a smart watch, a tablet, a laptop, or any other mobile computing device known to one of skill in the art.

The computing device 500 includes a controller 510 configured to control operations of the computing device 500. The controller 510 may be an electronic controller including a processor 530 and an associated memory 520 comprising computer-executable instructions (i.e., computer program product) that, when executed by the processor 530, cause the processor 530 to perform various operations. The processor 530 may be, but is not limited to, a single-processor or multi-processor system of any of a wide array of possible architectures, including field programmable gate array (FPGA), central processing unit (CPU), application specific integrated circuits (ASIC), digital signal processor (DSP) or graphics processing unit (GPU) hardware arranged homogenously or heterogeneously. The memory 520 may be but is not limited to a random access memory (RAM), read only memory (ROM), or other electronic, optical, magnetic or any other computer readable medium.

The computing device 500 includes a communication device 540 configured to communicate with the internet 306 through one or more wireless signals. The one or more wireless signals may include Wi-Fi, Bluetooth, BLE, Ultra-Wideband, Zigbee, Z-Wave, Sub-GHz RF Channel, cellular, satellite, or any other wireless signal known to one of skill in the art. The computing device 500 is configured to communicate with the cloud-based controller 340 through the internet 306. Alternatively, the computing device 500 may be connected to the internet 306 through a hardwired connection. The computing device 500 may be configured to communicate directly with the IAQ detector 310 through a short-range wireless signal 360, including, but not limited to, Wi-Fi, Bluetooth, BLE, Ultra-Wideband, Zigbee, Z-Wave, Sub-GHz RF Channel, or any other wireless communication method known to one of skill in the art.

The computing device 500 may include a display device 580, such as for example a computer display, an LCD display, an LED display, an OLED display, a touchscreen of a smart phone, tablet, or any other similar display device known to one of the skill in the art. A user operating the computing device 500 is able to view the computer application 550 through the display device 580.

The computing device 500 includes an input device 570 configured to receive a manual input from a user (e.g., human being) of computing device 500. The input device 570 may be a keyboard, a touch screen, a joystick, a knob, a touchpad, one or more physical buttons, a microphone configured to receive a voice command, a camera or sensor configured to receive a gesture command, an inertial measurement unit configured to detect a shake of the computing device 500, or any similar input device known to one of skill in the art. The user operating the computing device 500 is able to enter data into the computer application 550 through the input device 570. The input device 570 allows the user operating the computing device 500 to data into the computer application 550 via a manual input to input device 570. For example, the user may respond to a prompt on the display device 580 by entering a manual input via the input device 570. In one example, the manual input may be a touch on the touchscreen. In an embodiment, the display device 580 and the input device 570 may be combined into a single device, such as, for example, a touchscreen.

The computing device 500 may also include a feedback device 560. The feedback device 560 may activate in response to a manual input via the input device 570. The feedback device 560 may be a haptic feedback vibration device and/or a speaker emitting a sound. The feedback device 560 may activate to confirm that the manual input entered via the input device 570 was received via the computer application 550. For example, the feedback device 560 may activate by emitting an audible sound or vibrate the computing device 500 to confirm that the manual input entered via the input device 570 was received via the computer application 550.

The computing device 500 may also include a location determination device 590 that may be configured to determine a location of the computing device 500 using cellular signal triangulation, a global position satellite (GPS), or any location termination method known to one of skill in the art.

Each IAQ detector 310 is configured to detect an IAQ data set 384 within the room 412*a*, 412*b* throughout the day. The IAQ data set 384 may be detected in real-time at a selected frequency. The IAQ data set 384 may be captured at a plurality of time increments throughout the day. The IAQ data set 384 may be various measurements of air quality including but not limited to, particulate levels, CO2 levels, temperature, or any other IAQ parameter known to one of skill in the art. The IAQ data set 384 is then transmitted to the cloud-based controller 340 and the cloud-based controller 340 is configured to determine an IAQ health level 610 at each of the plurality of time increments 612 throughout the day based on the IAQ data set 384. The IAQ health level 610 may be a score of how healthy the air quality is within the room 412*a*, 412*b*. The IAQ health level 610 may be understood as the quality of the air experience by the individual 402.

The IAQ health level 610 may be specific each IAQ detector 310 and thus may be specific to the room 412*a*, 412*b* where the IAQ detector is located and may be displayed as a graph. FIG. 1 illustrates an IAQ health level graph 600*a* that displays the IAQ health level 610 detected within the first room 412*a* at over the plurality of time increments 612. FIG. 1 illustrates an IAQ health level graph 600*b* that displays the IAQ health level 610 detected within the second room 412*b* at over the plurality of time increments 612. The IAQ health level graph 600*a*, 600*b* may be visible via the computing device 500.

The IAQ devices 510*a*, 510*b* may be programed to turn on when an individual 402 enters the room 412*a*, 412*b* or will soon be entering the room 412*a*, 412*b* and then shut off when the individual 402 enters the room 412*a*, 412*b*. Thus, an IAQ health level 610 room may be allowed to degrade when an individual 402 leaves the room 412*a*, 412*b* as that individual 402 is not present. Therefore, looking at the IAQ health level 610 solely on a single room at a time basis may not give an accurate picture of the IAQ health level 610 experienced by an individual 402 as they come and go from the room 412*a*, 412*b* but rather it only gives an accurate picture of the IAQ health level 610 of that specific room.

The embodiment disclosed herein seek to rectify this problem by tracking the individual 402 as they move throughout the property 410 and combining IAQ health level 610 detected within each room 412*a*, 412*b* only while the individual was detected the room 412*a*, 412*b*.

Each IAQ detector 310 is configured to detect occupancy data 386 for a time period the individual 402 was located in a room 412*a*, 412*b*. The occupancy data 386 may be able to distinguish between different individuals 402 so that occupancy data 386 can be associated to a specific individual 402 and thus an IAQ health level 610 may also be associated with that specific individual 402.

In the example illustrated in FIG. 1, the individual 402 is detected by the first IAQ detector 310*a* to be in the first room

412*a* during a first time period T1, then the individual 402 is detected by the second IAQ detector 310*b* to be in the second room 412*b* during a second time period T2, and then the individual 402 is detected by neither the first IAQ detector 310*a* nor the second detector 310*b* and is believed to have left the property 410 during a third time period T3.

The cloud based controller 340 is then configured to combine the IAQ health level 610 for the first room 412*a* during the first time period T1 and the IAQ health level 610 for the second room 412*b* during the second time period T1 into a true IAQ health level graph 600*c* that only shows the IAQ heath level 610 experienced by the individual 402. Advantageously, by only showing the IAQ heath level 610 experienced by the individual 402, then the individual 402 has a better understanding of their own health over the course of the plurality of time increments 612. The true IAQ health level graph 600*c* may be accessible to the individual 402 through the computing device 500, wherein the true IAQ health level graph 600*c* may be displayed on the computing device 500.

An individual 402 may ask the voice activated assistant device 620 in an IAQ request 388 to provide the IAQ health level 610 using a voice command. The individual 402 may ask the voice activated assistant device 620 in an IAQ request 388 to provide the IAQ health level 610 for the specific room they are currently located in using a voice command and thus the IAQ detector system 300 will need to detect where the individual 404 is located based on wireless advertisement 382 detection, as previously discussed. The individual 402 may ask the voice activated assistant device 620 in an IAQ request 388 to provide the IAQ health level 610 for a specific room that they are not currently located in using a voice command.

Alternatively, the individual 402 may ask the voice activated assistant device 620 in an IAQ request 388 to provide the true IAQ health level 610 that they had experienced throughout the day or any other specific period of time.

Alternatively, the individual 402 may ask the voice activated assistant device 620 in an IAQ request 388 to provide the IAQ health level 610 that a second individual 404 is currently experiencing and thus the IAQ detector system 300 will need to detect where the second individual 404 is located based on wireless advertisement 382 detection of a second computing device 500*b* of a second individual 404, as previously discussed. The second computing device 500*b* may be a similar device to the computing device 500 with the same component or previous components as discussed previously. The second computing device 500*b* and second individual 404 is shown at a fourth time period T4.

Referring to FIG. 2, within continued references to FIG. 1, a flow diagram illustrating a method 800 of monitoring and reporting an IAQ level 610 is illustrated, in accordance with an embodiment of the present disclosure. In an embodiment, the method 800 may be performed by the cloud-based controller 340.

At block 804, an IAQ request 388 is received from a first individual 402 using a voice activated assistant device 620.

At block 806, a location of the first individual 402 is detected. The location including a room that the first individual 402 is located in. The location of the first individual 402 may be detected by detecting a wireless advertisement 382 of a computing device 500 of the first individual 402 using the IAQ detector 310. The wireless advertisement 382 may be a Bluetooth signal. The IAQ detector 310 may be located in a fire detector 311.

At block 808, an IAQ data set 384 is detected within the room.

At block 810, an IAQ health level 610 is determined based on the IAQ data set 384.

At block 812, the IAQ health level 610 is conveyed to the first individual 402. The IAQ health level 610 may be conveyed to the first individual 402 by audibly providing the IAQ health level 610 to the first individual 402 via the voice activated assistant device 620. The IAQ health level 610 may be conveyed to the first individual 402 by displaying the IAQ health level 610 on a computing device 500 of the first individual 402.

While the above description has described the flow process of FIG. 2 in a particular order, it should be appreciated that unless otherwise specifically required in the attached claims that the ordering of the steps may be varied.

Referring to FIG. 3, within continued references to FIG. 1, a flow diagram illustrating a method 900 of monitoring and reporting an IAQ level 610 is illustrated, in accordance with an embodiment of the present disclosure. In an embodiment, the method 900 may be performed by the cloud-based controller 340.

At block 904, an IAQ request 388 is received from a first individual 402 using a voice activated assistant device 620.

At block 906, a location of the second individual 404 is detected. The location including a room that the second individual 404 is located in. The location of the second individual 404 may be detected by detecting a wireless advertisement 382 of a computing device 500 of the second individual 404 using the IAQ detector 310. The wireless advertisement 382 may be a Bluetooth signal. The IAQ detector 310 may be located in a fire detector 311.

At block 908, an IAQ data set 384 is detected within the room.

At block 910, an IAQ health level 610 is determined based on the IAQ data set 384.

At block 912, the IAQ health level 610 is conveyed to the first individual 402. The IAQ health level 610 may be conveyed to the first individual 402 by audibly providing the IAQ health level 610 to the first individual 402 via the voice activated assistant device 620. The IAQ health level 610 may be conveyed to the first individual 402 by displaying the IAQ health level 610 on a computing device 500 of the first individual 402.

While the above description has described the flow process of FIG. 3 in a particular order, it should be appreciated that unless otherwise specifically required in the attached claims that the ordering of the steps may be varied.

The term "about" is intended to include the degree of error associated with measurement of the particular quantity based upon the equipment available at the time of filing the application. For example, "about" can include a range of ±8% or 5%, or 2% of a given value.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

As described above, embodiments can be in the form of processor-implemented processes and devices for practicing those processes, such as a processor. Embodiments can also be in the form of computer program code (e.g., computer program product) containing instructions embodied in tangible media (e.g., non-transitory computer readable medium), such as floppy diskettes, CD ROMs, hard drives, or any other non-transitory computer readable medium, wherein, when the computer program code is loaded into and executed by a computer, the computer becomes a device for practicing the embodiments. Embodiments can also be in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes a device for practicing the exemplary embodiments. When implemented on a general-purpose microprocessor, the computer program code segments configure the microprocessor to create specific logic circuits.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A method of monitoring and reporting an environmental parameter, the method comprising:

receiving a request for the environmental parameter from a first individual using a voice activated assistant device;

detecting a location of the first individual, the location including a room that the first individual is located in, wherein detecting the location of the first individual is performed by an environmental sensor detecting a wireless advertisement of a computing device of the first individual;

detecting the environmental parameter using the environmental sensor nearest to the first individual; and conveying the environmental parameter to the first individual using the voice activated assistant device;

wherein the environmental sensor includes one or more of a smoke detector, fire detector, carbon monoxide detector and an indoor air quality detector;

the method further comprising:

tracking the location of the first individual;

detecting the environmental parameter in a first room for a first time period in response to detecting the first individual being located in the first room;

detecting the environmental parameter in a second room for a second time period in response to detecting the first individual being located in the second room;

combining (i) the environmental parameter in the first room for the first time period and (ii) the environmental parameter in the second room for the second time period into a combined environmental parameter graph indicating the environmental parameter experienced by the first individual over the first time period and the second time period;

providing the combined environmental parameter graph to the first individual.

2. The method of claim 1, wherein the conveying environmental parameter to the first individual further comprises:

audibly providing the environmental parameter to the first individual via the voice activated assistant device.

3. The method of claim 1, wherein the conveying the environmental parameter to the first individual further comprises:

displaying the environmental parameter on the computing device of the first individual.

4. The method of claim 1, wherein the wireless advertisement is a Bluetooth signal.

5. A method of monitoring and reporting an environmental parameter, the method comprising:

receiving a request for the environmental parameter from a first individual using a voice activated assistant device;

detecting a location of a second individual, the location including a room that the second individual is located in, wherein detecting the location of the second individual is performed by an environmental sensor detecting a wireless advertisement of a computing device of the second individual using the environmental sensor;

detecting the environmental parameter using an environmental sensor nearest to the second individual; and conveying the environmental parameter to the first individual using the voice activated assistant device;

wherein the environmental sensor includes one or more of a smoke detector, fire detector, carbon monoxide detector and an indoor air quality detector;

the method further comprising:

tracking the location of the second individual;

detecting the environmental parameter in a first room for a first time period in response to detecting the second individual being located in the first room;

detecting the environmental parameter in a second room for a second time period in response to detecting the second individual being located in the second room;

combining (i) the environmental parameter in the first room for the first time period and (ii) the environmental parameter in the second room for the second time period into a combined environmental parameter graph indicating the environmental parameter experienced by the second individual over the first time period and the second time period;

providing the combined environmental parameter graph to the first individual.

6. The method of claim 5, wherein the conveying the environmental parameter to the first individual further comprises:

audibly providing the environmental parameter to the first individual via the voice activated assistant device.

7. The method of claim 5, wherein the conveying the environmental parameter to the first individual further comprises:

displaying the environmental parameter on the computing device of the first individual.

8. The method of claim 5, wherein the wireless advertisement is a Bluetooth signal.

9. A computer program product tangibly embodied on a non-transitory computer readable medium, the computer program product including instructions that, when executed by a processor, cause the processor to perform operations comprising:

receiving a request for an environmental parameter from a first individual using a voice activated assistant device;

detecting a location of the first individual, the location including a room that the first individual is located in, wherein detecting the location of the first individual is performed by an environmental sensor detecting a wireless advertisement of a computing device of the first individual;

detecting the environmental parameter the environmental sensor nearest to the first individual; and conveying the environmental parameter to the first individual using the voice activated assistant device;

wherein the environmental sensor includes one or more of a smoke detector, fire detector, carbon monoxide detector and an indoor air quality detector;

the operations further comprising:

tracking the location of the first individual;

detecting the environmental parameter in a first room for a first time period in response to detecting the first individual being located in the first room;

detecting the environmental parameter in a second room for a second time period in response to detecting the first individual being located in the second room;

combining (i) the environmental parameter in the first room for the first time period and (ii) the environmental parameter in the second room for the second time period into a combined environmental parameter graph indicating the environmental parameter experienced by the first individual over the first time period and the second time period;

providing the combined environmental parameter graph to the first individual.

10. The computer program product of claim 9, wherein the conveying the environmental parameter to the first individual further comprises:

audibly providing the environmental parameter to the first individual via the voice activated assistant device.

11. The computer program product of claim 9, wherein the conveying the environmental parameter to the first individual further comprises:

displaying the environmental parameter on the computing device of the first individual.

12. The computer program product of claim 9, wherein the wireless advertisement is a Bluetooth signal.

* * * * *